(12) United States Patent
Larson-Smith et al.

(10) Patent No.: US 8,709,545 B2
(45) Date of Patent: Apr. 29, 2014

(54) HYBRID COATINGS AND ASSOCIATED METHODS OF APPLICATION

(75) Inventors: Kjersta L. Larson-Smith, Seattle, WA (US); Kay Y. Blohowiak, Issaquah, WA (US); Jill E. Seebergh, Seattle, WA (US); Michael R. Sirkis, Everett, WA (US); Vasan S. Sundaram, Issaquah, WA (US)

(73) Assignee: The Boeing Company, Chicago, IL (US)

( * ) Notice: Subject to any disclaimer, the term of this patent is extended or adjusted under 35 U.S.C. 154(b) by 519 days.

(21) Appl. No.: 12/363,085

(22) Filed: Jan. 30, 2009

(65) Prior Publication Data

US 2010/0196621 A1    Aug. 5, 2010

(51) Int. Cl.
*B05D 3/02* (2006.01)
(52) U.S. Cl.
USPC ............... 427/387; 427/535; 427/536
(58) Field of Classification Search
USPC ................. 427/387, 535, 536
See application file for complete search history.

(56) References Cited

U.S. PATENT DOCUMENTS

| | | | |
|---|---|---|---|
| 5,928,527 A * | 7/1999 | Li et al. ................... | 216/67 |
| 6,096,469 A | 8/2000 | Anderson et al. | |
| 6,536,604 B1 * | 3/2003 | Brinker et al. ............... | 210/490 |
| 2003/0211330 A1 | 11/2003 | Anderson et al. | |
| 2004/0099183 A1 | 5/2004 | Wire et al. | |
| 2004/0107989 A1 | 6/2004 | Woll et al. | |
| 2007/0196633 A1 * | 8/2007 | Coak et al. .................... | 428/215 |
| 2008/0111027 A1 | 5/2008 | Blohowiak et al. | |
| 2008/0137206 A1 * | 6/2008 | Nakamura et al. ............ | 359/601 |
| 2009/0148711 A1 * | 6/2009 | Le Blanc et al. .............. | 428/447 |

FOREIGN PATENT DOCUMENTS

WO    WO 2007003828 A2 *   1/2007   ............... C09D 5/08

OTHER PUBLICATIONS

Chai et al. Wettability Interpretation of Oxygen Plasma Modified Poly(methyl methacrylate) Langmuir, 2004, 20 (25), 10919-10927.*
Liu et al., "An aqueous sol-gel route to prepare organic-inorganic hybrid materials," *Journal of Materials Chemistry*, 17, pp. 4430-4435 (2007).
PCT, International Search Report and Written Opinion, International Application No. PCT/US2009/063401; 10 pages (Feb. 12, 2010).

* cited by examiner

*Primary Examiner* — Robert S Walters Jr.
(74) *Attorney, Agent, or Firm* — Diane M. Tsuda

(57) ABSTRACT

A hybrid coating including a mixture of an organosilane component, a metal alkoxide component and a surfactant component. A method for coating a substrate including cleaning a substrate surface, treating the surface with oxygen plasma, applying an adhesion promoter to the surface, then applying a hybrid coating to the surface and curing the hybrid coating. A method for making a hybrid coating includes preparing a mixture comprising an organosilane, a metal alkoxide and a surfactant, heating the mixture; and filtering the mixture.

14 Claims, 8 Drawing Sheets

HYBRID COATINGS AND ASSOCIATED METHODS OF APPLICATION

FIELD

The present patent application relates to hybrid abrasion resistant coatings, methods for making the hybrid abrasion coatings, and associated methods for treating and replenishing surfaces subject to wear.

BACKGROUND

The effects of wear on mechanical parts and exposed surfaces are prevalent in various applications. The effects of wear are particularly prevalent in connection with transparent parts and surfaces that require clarity. For example, the windows of aircraft are subjected to wear both in flight and on the ground.

Accordingly, scientists and engineers continue to search for coatings that resist the effects of wear, thereby reducing the time and expense associated with maintenance by extending the time intervals between successive replacement/repair operations. Furthermore, scientists and engineers continue to search for coatings that may be used to restore scratched and worn substrates, thereby reducing maintenance costs by facilitating the repair of substrates that would otherwise require replacement. Environmentally friendly coatings would be particularly attractive.

SUMMARY

In one aspect, the disclosed hybrid coating may include a mixture of an organosilane component, a metal alkoxide component and a surfactant component. In a more specific aspect, the mixture may be substantially free of particles greater than about 11 μm.

In another aspect, the disclosed hybrid coating may include a mixture of (3-glycidoxypropyl)trimethoxysilane, aluminum s-butoxide and a surfactant component, wherein the mixture is substantially free of particles greater than about 11 μm.

In another aspect, the disclosed method for making a hybrid coating may include the steps of combining an organosilane, a metal alkoxide and a surfactant to form a mixture, heating the mixture and, after the heating step, filtering the mixture.

In another aspect, the disclosed method for coating a substrate may include the steps of cleaning a surface of the substrate, treating the surface with oxygen plasma, applying an adhesion promoter to the surface, applying a hybrid coating to the surface, the hybrid coating including an organosilane component, a metal alkoxide component and a surfactant component, and curing the hybrid coating.

Other aspects of the disclosed hybrid coatings and associated methods of application will become apparent from the following description, the accompanying drawings and the appended claims.

DETAILED DESCRIPTION

Figure 1:
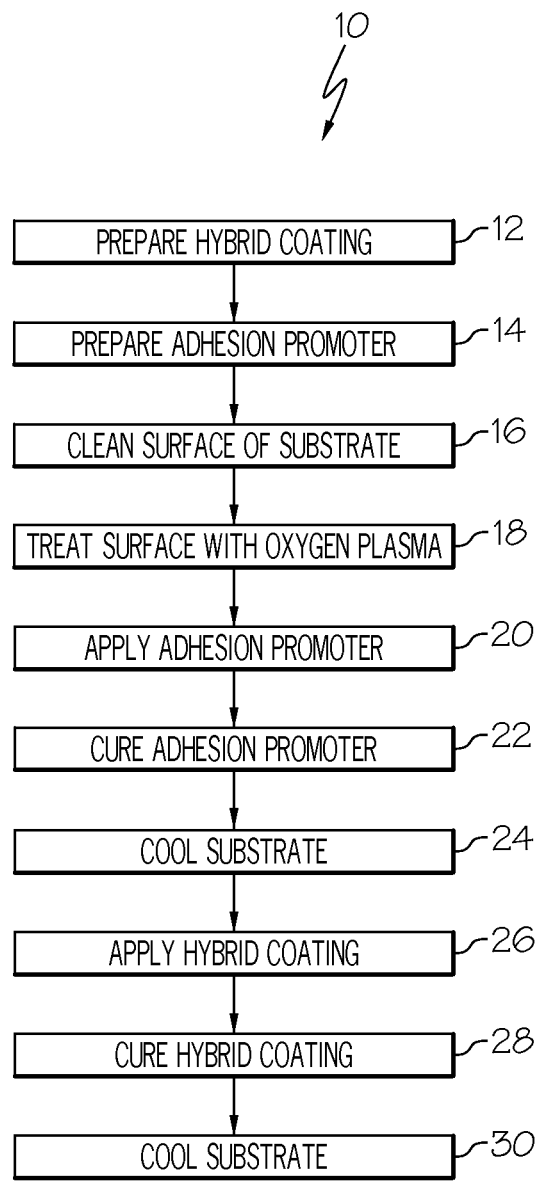
FIG. 1 is a flow chart illustrating one exemplary method for applying the disclosed hybrid coating.

In one aspect, the disclosed hybrid coating may include an organosilane component, a metal alkoxide component and a surfactant component. Water may be added to, for example, adjust the solids content and/or viscosity of the mixture. Additional components having various functionalities, such as, for example, dyes, light scavengers, rheology modifiers and biocides, may be added to the disclosed hybrid coating without departing from the scope of the present disclosure.

The organosilane component may be the organic portion of the disclosed hybrid coating. In one exemplary aspect, the organosilane component may be (3-glycidoxypropyl)trimethoxysilane. However, alternative examples of compounds useful as the organosilane component include 3-glycidoxypropyltriethoxysilane, p-aminophenylsilane, allyltrimethoxysilane, n-(2-aminoethyl)-3-aminopropyltrimethoxysilane, 3-aminopropyltriethoxysilane, 3-aminopropyltrimethoxysilane, 3-glycidoxypropyldiisopropylethoxysilane, (3-glycidoxypropyl)methyldiethoxysilane, 3-mercaptopropyltrimethoxysilane, 3-mercaptopropyltriethoxysilane, 3-methacryloxypropylmethyldiethoxysilane, 3-methacryloxypropylmethyldimethoxysilane, 3-methacryloxypropyltrimethoxysilane, n-phenylaminopropyltrimethoxysilane, vinylmethyldiethoxysilane, vinyltriethoxysilane, vinyltrimethoxysilane and tetraethylorthosilicate, as well as combinations thereof. Those skilled in the art will appreciate that other compounds may be used as the organosilane component of the disclosed hybrid coating without departing from the scope of the present disclosure.

The metal alkoxide component may be the inorganic portion of the disclosed hybrid coating. In one exemplary aspect, the metal alkoxide component may be an aluminum alkoxide, such as aluminum s-butoxide, aluminum n-butoxide and aluminum t-butoxide. In a second exemplary aspect, the metal alkoxide component may be a cerium alkoxide, such as cerium IV isopropoxide, cerium IV methoxyethoxide and cerium III 2,4-pentanedionate. Those skilled in the art will appreciate that other metal alkoxides may be used as the metal alkoxide component of the disclosed hybrid coating without departing from the scope of the present disclosure.

Thus, the disclosed hybrid coating may be a hybrid material that includes both an organic component and an inorganic component.

Without being limited to any particular theory, the surfactant component of the disclosed hybrid coating may improve the wet adhesion of the coating by reducing the surface tension of the coating. In one exemplary aspect, the surfactant component may be a liquid, nonionic surfactant, such as a straight chain primary aliphatic alkoxylated alcohol. A specific example of such a surfactant is ANTAROX® BL-240 (CAS#68603-25-8), available from Rhodia Operations of Aubervilliers, France. However, those skilled in the art will appreciate that other surfactants may be used as the surfactant component of the disclosed hybrid coating without departing from the scope of the present disclosure.

The relative quantities of the organosilane, metal alkoxide and surfactant components may be selected to optimize the abrasion resistance, clarity, surface wetting, curability or other physical properties of the disclosed hybrid coating. In one exemplary aspect, the metal alkoxide and organosilane components may be present in the disclosed coating at a molar ratio of about 2:1 (2 moles of the metal alkoxide component to 1 mole of the organosilane component) and the surfactant component may be present at a molar ratio of 75:1 with respect to the metal alkoxide component (75 moles of the metal alkoxide component to 1 mole of the surfactant component). However, those skilled in the art will appreciate that the quantities (or molar ratios) may vary depending on the constituents, the physical properties being optimized, or the specific needs of the user.

In one aspect, the disclosed hybrid coating may be prepared by combining appropriate quantities of the organosilane, metal alkoxide and surfactant components, optionally with a sufficient quantity of water, in a mixing vessel. The composition may be heated while continuously stirring until the solution becomes clear. The clear solution may be cooled to room temperature (e.g., about 25° C.) and then filtered. In one particular aspect, the filtering step may be performed to remove particles greater than about 10 μm. For example, Whatman #1 qualitative filter paper, which has a manufacturer stated particle retention rating of 11 μm, may be used.

At this point, those skilled in the art will appreciate that the resulting clear, cooled and filtered liquid may be a sol gel.

EXAMPLE 1

Hybrid Coating

A hybrid coating is prepared by combining 11.7 milliliters of 75 percent aluminum s-butoxide in s-butanol, 15.1 milliliters of (3-glycidoxypropyl)trimethoxysilane, 0.5 milliliters of 10 weight percent ANTAROX® BL-240, and 22.7 milliliters of deionized water in a heat resistant vessel. The mixture is heated to a temperature of 90° C. while stirring. Stirring continues for an additional 120 minutes or until the mixture is clear. The mixture is then removed from the heat source and allowed to cool to 25° C. The cooled mixture is then passed through Whatman #1 qualitative filter paper and the filtrand is discarded. The filtrate is stored in an air-tight container.

As discussed below, the disclosed hybrid coating may be used to coat various substrates, such as acrylic (e.g., stretched acrylic) and glass, as an initial coating or as a replenishment coating. Those skilled in the art will appreciate that substrates other than acrylic and glass may be coated with the disclosed hybrid coating without departing from the scope of the present disclosure.

Referring to FIG. 1, one method for applying a hybrid coating, generally designated 10, may begin by preparing the disclosed hybrid coating, as shown in block 12. The preparation of the disclosed hybrid coating has been described in detail above.

As shown in block 14, an adhesion promoter may be prepared. The adhesion promoter may be any material that may promote the adhesion of the disclosed hybrid coating to the underlying substrate. One exemplary adhesion promoter includes 2.5 percent by weight 3-aminopropyltriethoxysilane in water. However, those skilled in the art will appreciate that various adhesion promoting compositions may be used.

As shown in block 16, the surface of the substrate that will receive the coating may be properly cleaned. Various techniques for cleaning surfaces that will receive coatings are well known in the art. For example, when the substrate is stretched acrylic, the surface of the substrate may be wiped with isopropyl alcohol.

Furthermore, as shown in block 18, the cleaned surface of the substrate may be treated with oxygen plasma, though other treatments such as corona may be used without departing from the scope of the present disclosure. The oxygen plasma may be generated with an open air plasma treat system and may have a head that travels about 0.1 inches per second at a distance of about 0.75 inches from the surface of the substrate. As an example, the oxygen plasma may be generated using the SPI Plasma-Prep™ plasma etcher available from Structure Probe, Inc. of West Chester, Pa. Without being limited to any particular theory, it is believed that the oxygen plasma and the surfactant in the disclosed hybrid coating both contribute to improving the wettability and the adhesion of the hybrid coating to the substrate.

After the cleaning (block 16) and plasma treating (block 18) steps, the adhesion promoter may be applied to the surface of the substrate, as shown in block 20. While various techniques may be used to apply the adhesion promoter, one exemplary technique is spraying. Then, as shown in block 22, the adhesion promoter may be allowed to cure if necessary. For example, when a 2.5 percent by weight solution of 3-aminopropyltriethoxysilane in water is used as the adhesion promoter, the adhesion promoter may be cured for 10 minutes at 80° C., after which the substrate may be allowed to cool (block 24).

At this point, those skilled in the art will appreciate that the steps shown in blocks 14 through 24 may be omitted as desired. In particular, the use of an adhesion promoter (i.e., the steps shown in blocks 14, 20, 22 and 24) may be optionally omitted when the disclosed hybrid coating is used as a replenishing coating. Also, the oxygen plasma treatment (block 18) may be optionally omitted when the disclosed hybrid coating is used as a replenishing coating.

As shown in block 26, the hybrid coating may be applied to the surface of the cleaned and treated substrate. While spraying the hybrid coating onto the substrate is one appropriate application technique, those skilled in the art will appreciate that various application techniques, such as drawing, blade coating and painting, may be used without departing from the scope of the present disclosure.

As shown in block 28, the hybrid coating applied to the substrate may be cured before entering service. While the curing technique, including the curing time and curing temperature, may vary depending on the specific composition of the hybrid coating, if the hybrid coating described in Example 1 above is used, a suitable cure should be obtained by resting at room temperature for about 16 hours followed by curing at 80° C. for about 2 hours. After curing, the coated substrate may be allowed to cool, as shown in block 30.

Hybrid coatings ("Hybrid") were tested on stretched acrylic for wet and dry adhesion in accordance with BSS7225, Class 5 (adhesion of 7 is the minimum requirement and 10 is perfect adhesion). Aluminum s-butoxide was used as the metal alkoxide component ("Inorganic"), (3-glycidoxypropyl)trimethoxysilane was used as the organosilane component ("Organic") and ANTAROX® BL-240 was used as the surfactant component. Oxygen plasma ("Plasma"), corona treatment ("Corona") and an adhesion promoter ("AP") were used where indicated. The results are shown in Table 1.

TABLE 1

| Stack Up | Organic to Inorganic Ratio | Plasma Speed (in/s) | Plasma Height (in) | Dry Adhesion | Wet Adhesion |
| --- | --- | --- | --- | --- | --- |
| Hybrid (only) | 2 | 0 | 0 | 1 | 1 |
| Corona + AP + Hybrid | 2 | (60 s) | 2 | 10 | 3 |
| Plasma + AP + Hybrid | 2 | 0.5 | 0.4 | 8 | 5 |
| Plasma + AP + Hybrid | 2 | 0.25 | 0.7 | 9 | 8 |
| Plasma + AP + Hybrid | 2 | 0.1 | 0.7 | 10 | 10 |
| Plasma + AP + Hybrid | 2 | 0.05 | 0.7 | 10 | 10 |
| Plasma + AP + Hybrid | 4 | 0.1 | 0.7 | 2 | 1 |

Thus, the disclosed hybrid coatings yield good dry and wet adhesion, particularly when applied using the disclosed methods.

Filtered and unfiltered hybrid coatings having aluminum s-butoxide to ANTAROX® BL-240 ratios of 150:1 and 75:1 were tested on stretched acrylic for haze and clarity. The results are shown in Table 2.

TABLE 2

| Sample | Filtered | Inorganic to Surfactant Ratio | Haze | Standard | Clarity | Standard |
| --- | --- | --- | --- | --- | --- | --- |
| 1 | No | 150:1 | 2.05 | <1.0 | 98.2 | >99.0 |
| 2 | Yes | 150:1 | 1.51 | <1.0 | 98.5 | >99.0 |
| 3 | No | 75:1 | 1.25 | <1.0 | 99.6 | >99.0 |
| 4 | Yes | 75:1 | 0.22 | <1.0 | 99.8 | >99.0 |

Thus, the disclosed hybrid coatings yield low initial haze and high initial clarity.

The abrasion resistance of the disclosed hybrid coatings on stretched acrylic was assessed using ASTM D 1044, which is commonly referred to as the Taber abrasion test. The results are shown in FIGS. 2-7.

Figure 2:
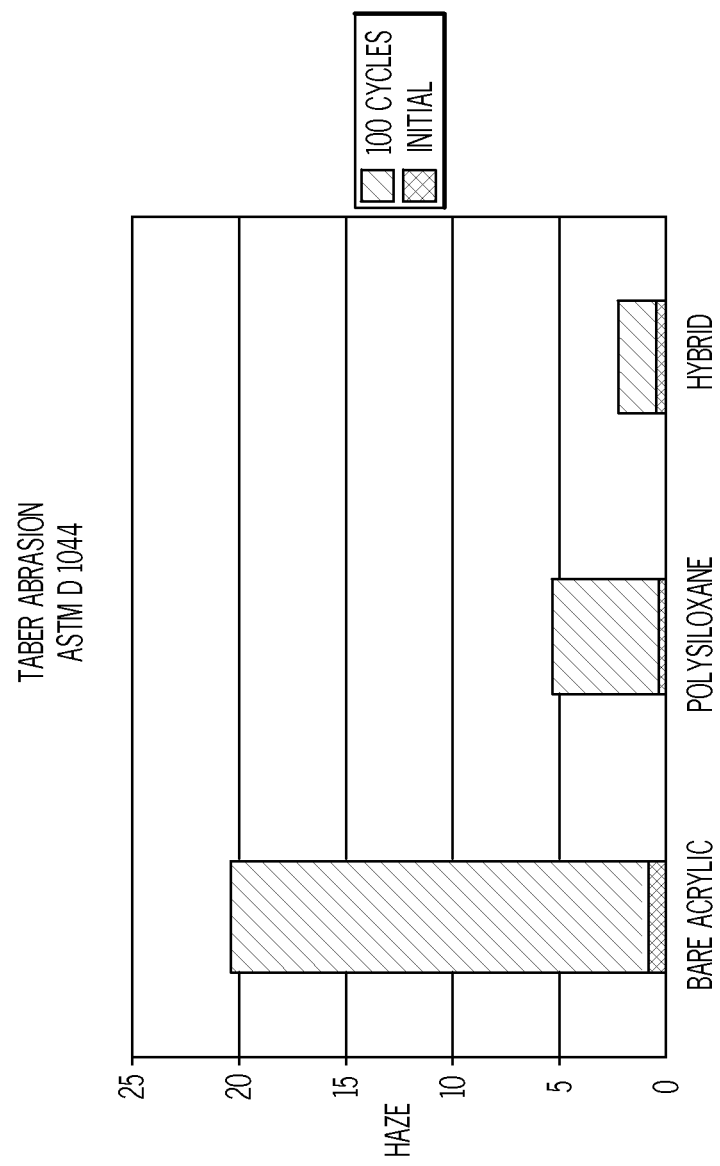
FIG. 2 is a graphical illustration of percent haze obtained after 100 cycles of Taber abrasion on an untreated substrate ("Bare Acrylic"), a substrate treated with a prior art coating ("Polysiloxane"), and a substrate treated with an aspect of the disclosed hybrid coating ("Hybrid")
Figure 3:
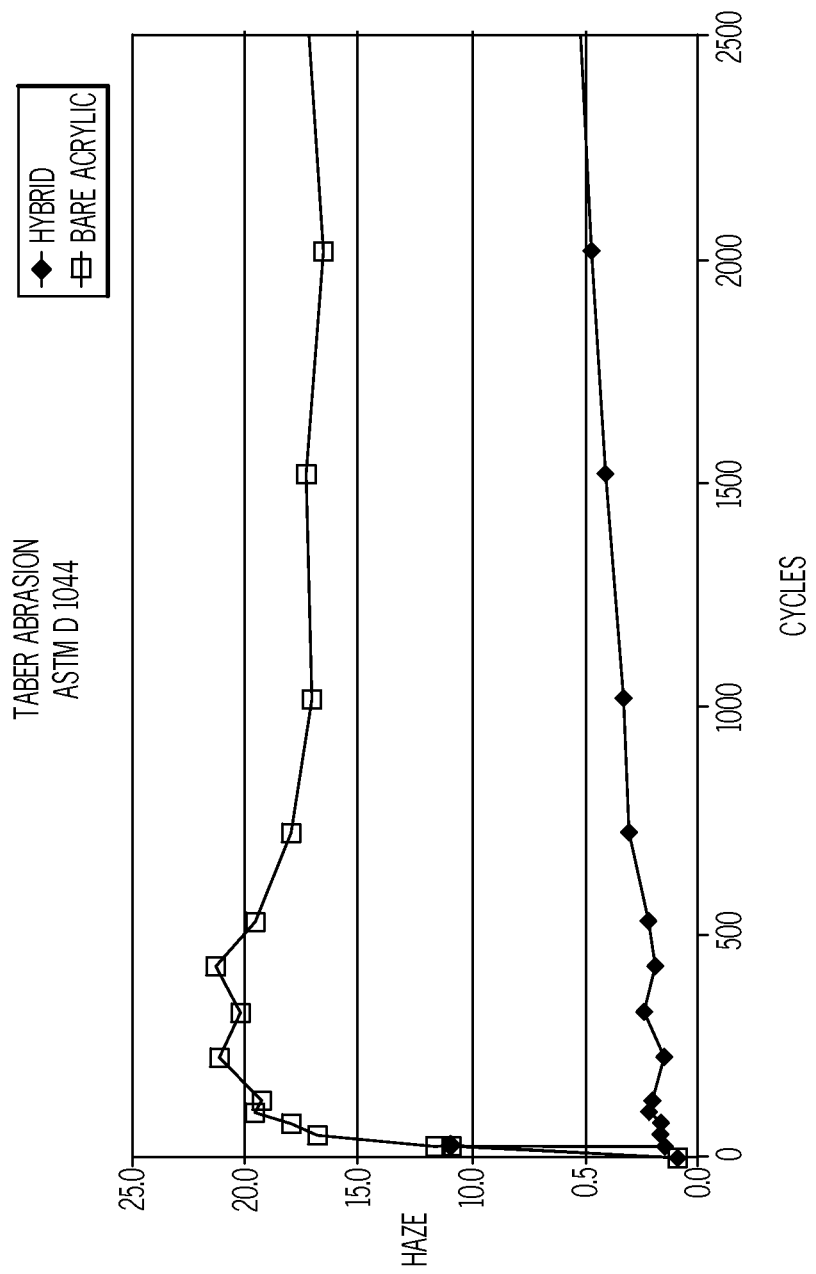
FIG. 3 is a graphical illustration of percent haze versus number of Taber abrasion cycles for a bare acrylic substrate and an acrylic substrate coated with the disclosed hybrid coating.
Figure 4:
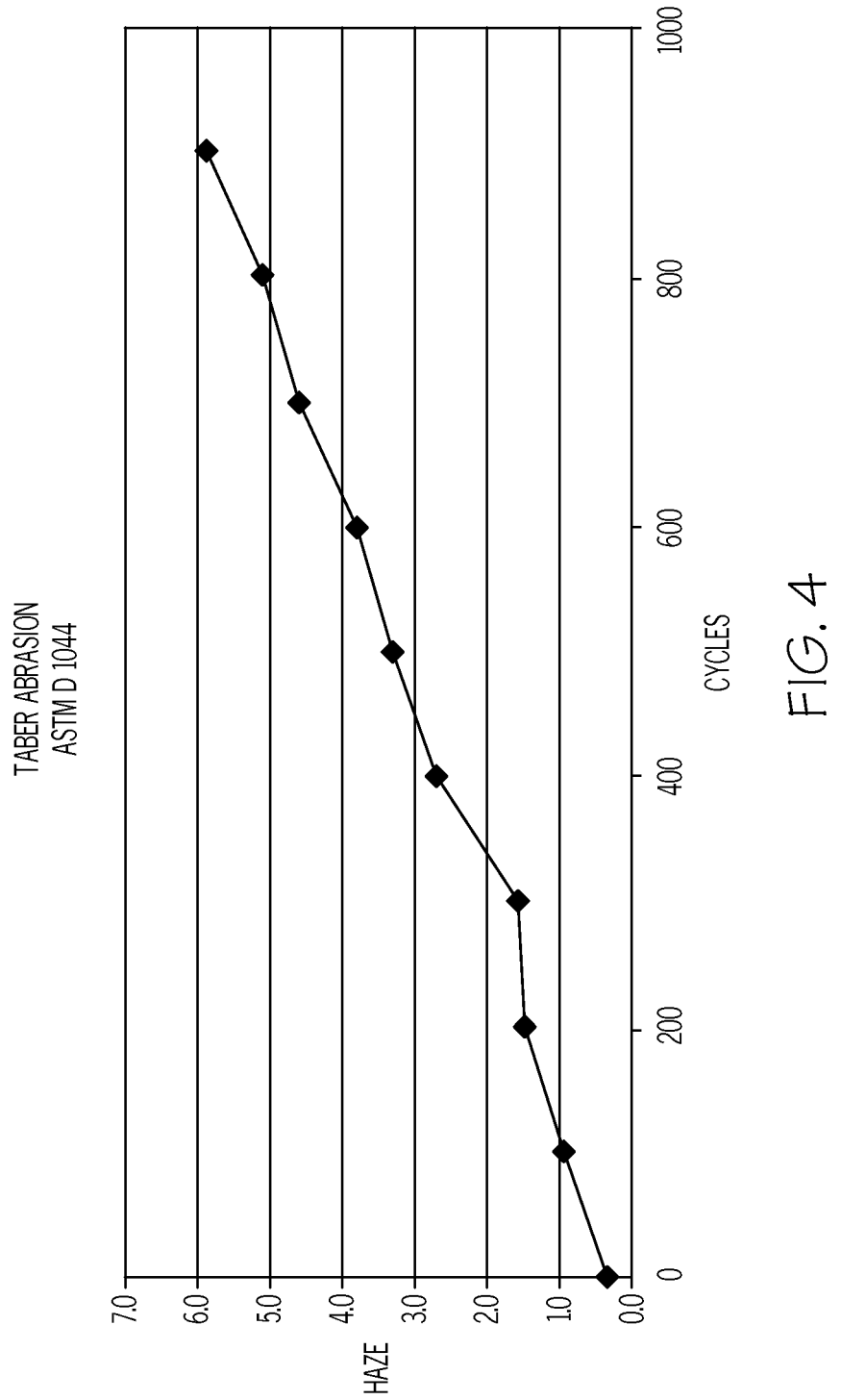
FIG. 4 is a graphical illustration of percent haze versus number of Taber abrasion cycles for an worn acrylic substrate replenished with the disclosed hybrid coating.
Figure 5:
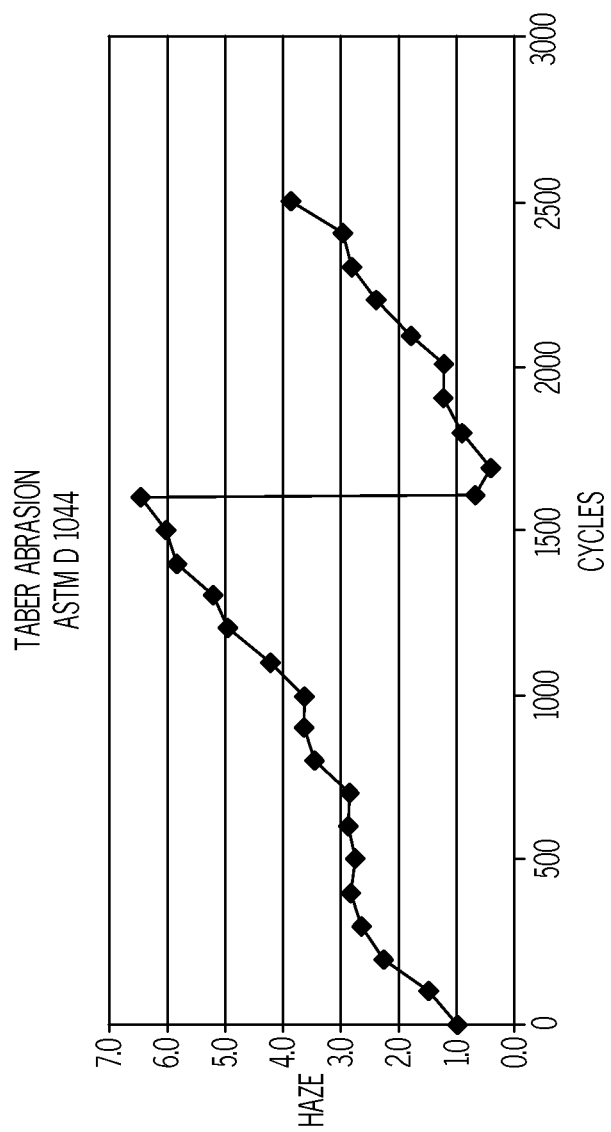
FIG. 5 is a graphical illustration of percent haze versus number of Taber abrasion cycles for an acrylic substrate coated with the disclosed hybrid coating, subjected to abrasion, replenished with the disclosed hybrid coating, then again subjected to abrasion.
Figure 6:
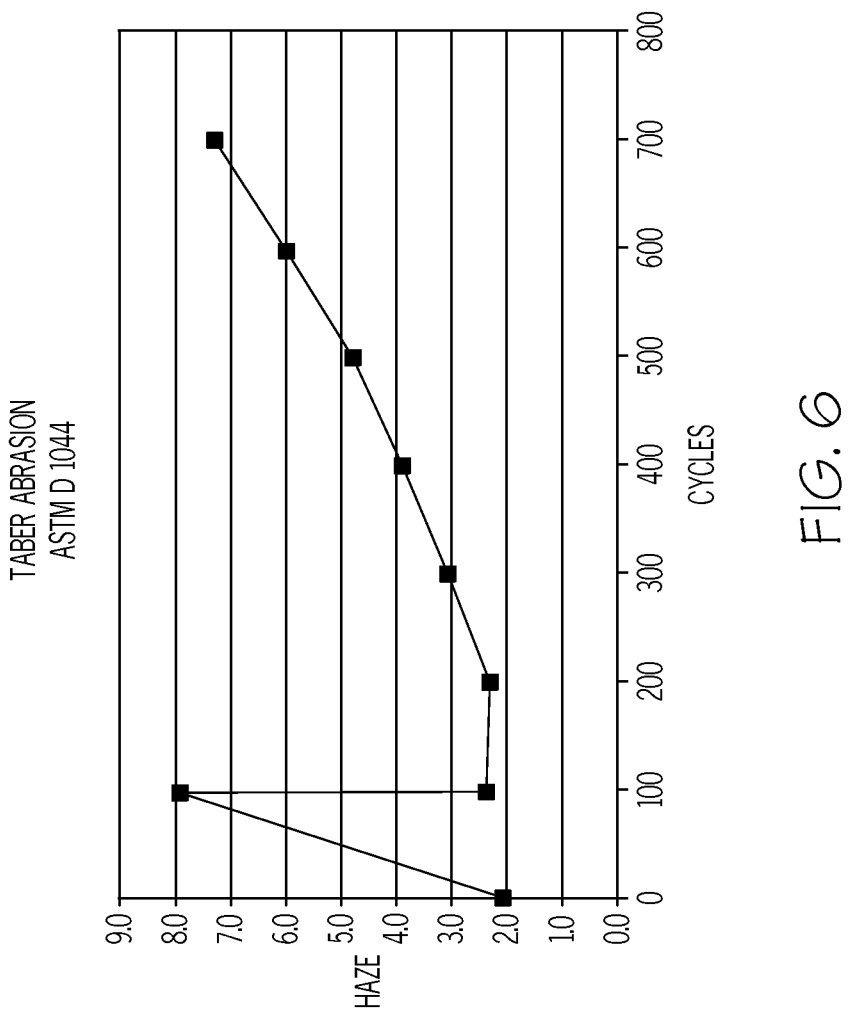
FIG. 6 is a graphical illustration of percent haze versus number of Taber abrasion cycles for an acrylic substrate coated with a prior art coating, subjected to abrasion, replenished with the disclosed hybrid coating, then again subjected to abrasion.
Figure 7:
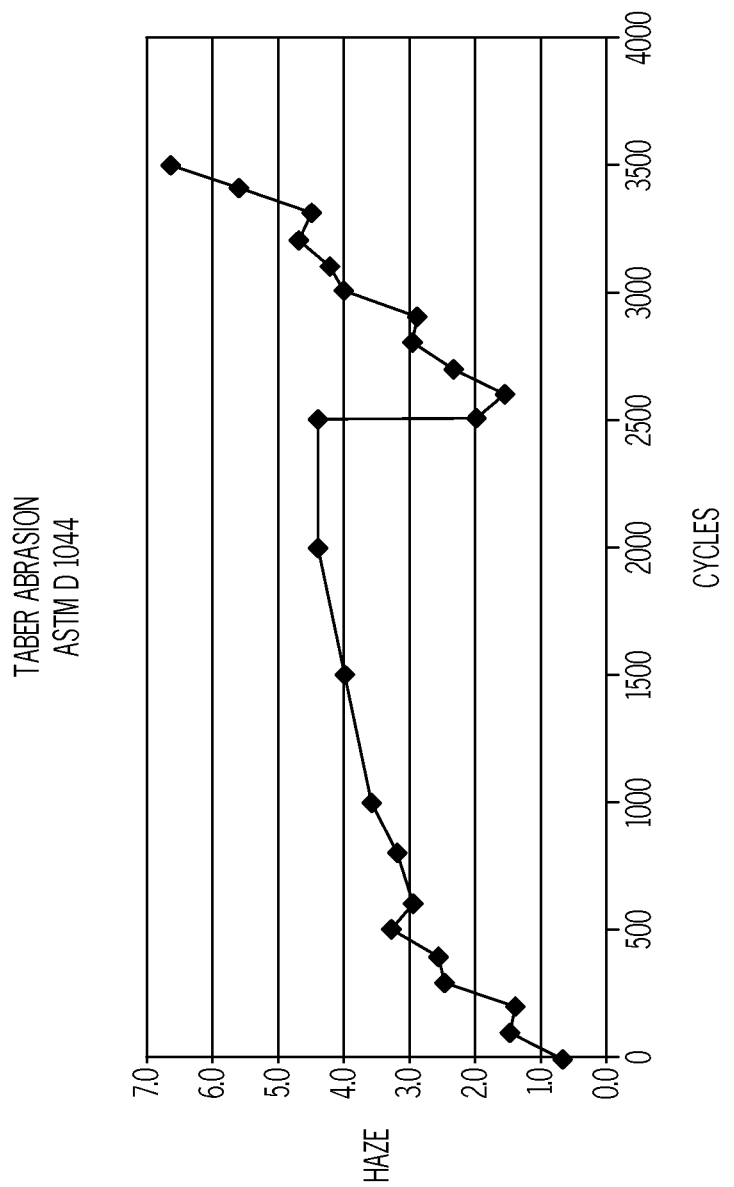
FIG. 7 is a graphical illustration of percent haze versus number of Taber abrasion cycles for an acrylic substrate initially coated with a duplex coating (i.e., a first layer of prior art coating with a top coat of the disclosed hybrid coating), subjected to abrasion, replenished with the disclosed hybrid coating, then again subjected to abrasion.
Figure 8:
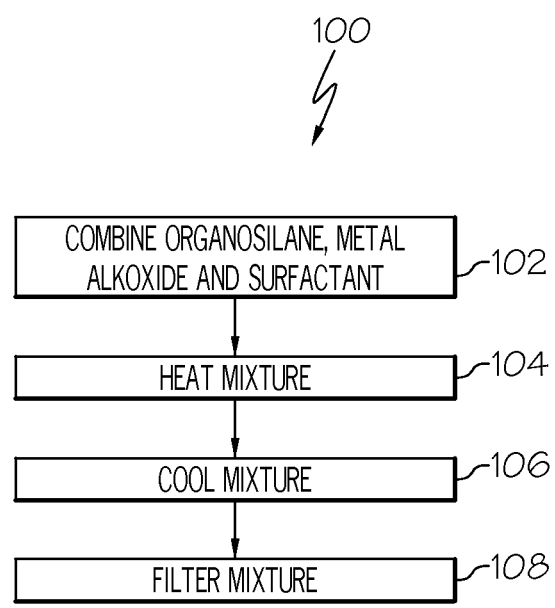
FIG. 8 is a flow chart illustrating one exemplary method for making the disclosed hybrid coating.

FIG. 2 shows percent haze obtained after 100 cycles of abrasion on bare acrylic, acrylic treated with a polysiloxane only (prior art), and acrylic treated with the disclosed hybrid coating. FIG. 3 shows percent haze versus abrasion cycles for a bare acrylic substrate and an acrylic substrate coated with the disclosed hybrid coating. FIG. 4 shows percent haze versus abrasion cycles for a worn acrylic substrate replenished with the disclosed hybrid coating. FIG. 5 shows percent haze versus abrasion cycles for an acrylic substrate coated with the disclosed hybrid coating, subjected to approximately 1600 abrasion cycles, replenished with the disclosed hybrid coating, then again subjected to abrasion. FIG. 6 shows percent haze versus abrasion cycles for an acrylic substrate coated with a prior art coating, subjected to approximately 100 abrasion cycles, replenished with the disclosed hybrid coating, then again subjected to abrasion. FIG. 7 shows percent haze versus abrasion cycles for an acrylic substrate initially coated with a duplex coating (i.e., a first layer of prior art coating with a top coat of the disclosed hybrid coating), subjected to approximately 2500 abrasion cycles, replenished with the disclosed hybrid coating, then again subjected to abrasion.

Thus, the disclosed hybrid coatings provide substantially improved abrasion resistance, whether used as an initial coating or as a replenishing coating.

Accordingly, the disclosed hybrid coatings yield low initial haze and high initial clarity, good dry and wet adhesion (particularly to stretched acrylic), and excellent abrasion resistance. Furthermore, the disclosed hybrid coatings may be used as replenishment coatings to restore the clarity and abrasion resistance to worn substrates, regardless of whether the substrates have been previously coated. Still furthermore, the disclosed hybrid coatings may be prepared as an aqueous sol-gel material and, therefore, are environmentally friendly.

Although various aspects of the disclosed hybrid coatings and associated methods of application have been shown and described, modifications may occur to those skilled in the art upon reading the specification. The present application includes such modifications and is limited only by the scope of the claims.

What is claimed is:

1. A method of replenishing a worn substrate comprising the steps of:
cleaning a surface of said worn substrate;
treating said surface with oxygen plasma;
after said treating step, applying an adhesion promoter to said surface;
after said step of applying said adhesion promoter, applying a hybrid coating mixture to said surface to form a hybrid coating, said hybrid coating including an organosilane component, a metal alkoxide component and a surfactant component; and
curing said hybrid coating to restore clarity and abrasion resistance to said worn substrate;
wherein said worn substrate is a transparent part having an optical clarity acceptable for a window;
wherein said metal alkoxide component is present in said mixture at a molar ratio of about 75:1 with respect to said surfactant component, and after curing the hybrid coating has an initial clarity greater than 98.

2. The method of claim 1 wherein said worn substrate is a stretched acrylic, transparent part.

3. The method of claim 1 wherein said step of treating said worn surface with oxygen plasma comprises generating oxygen plasma with an open air plasma treatment system wherein the treatment system includes a head that travels about 0.1 inches per second at a distance of about 0.75 inches from said surface.

4. The method of claim 1 wherein said adhesion promoter includes a solution of 3-aminopropyltriethoxysilane in water.

5. The method of claim 1 further comprising the step of curing said adhesion promoter.

6. The method of claim 1 further comprising the step of filtering said hybrid coating mixture prior to application.

7. The method of claim 6 wherein said hybrid coating mixture is heated prior to said filtering step.

8. The method of claim 1 wherein said organosilane component includes (3-glycidoxypropyl) trimethoxysilane and said metal alkoxide component includes aluminum s-butoxide.

9. The method of claim 1 wherein said hybrid coating mixture is substantially free of particles greater than 11 μm.

10. The method of claim 1 wherein said organosilane component is selected from the group consisting of (3-glycidoxypropyl)trimethoxysilane, 3-glycidoxypropyltriethoxysilane, paminophenylsilane, allyltrimethoxysilane, n-(2- aminoethyl)-3-aminopropyltrimethoxysilane, 3-aminopropyltriethoxysilane, 3-aminopropyltrimethoxysilane, 3-glycidoxypropyldiisopropylethoxysilane, (3-glycidoxypropyl)methyldiethoxysilane, 3-mercaptopropyltrimethoxysilane, 3-mercaptopropyltriethoxysilane, 3-methacryloxypropylmethyldiethoxysilane, 3-methacryloxypropylmethyldimethoxysilane, 3methacryloxypropyltrimethoxysilane, n-phenylaminopropyltrimethoxysilane, vinylmethyldiethoxysilane, vinyltriethoxysilane, vinyltrimethoxysilane, tetraethylorthosilicate and mixtures thereof.

11. The method of claim 1 wherein said metal alkoxide is selected from the group consisting of aluminum s-butoxide, aluminum n-butoxide and aluminum t-butoxide.

12. The method of claim 1 wherein said metal alkoxide is selected from the group consisting of cerium IV isopropoxide, cerium IV methoxyethoxide and cerium III 2,4-pentanedionate.

13. The method of claim 1 wherein said surfactant component includes a straight chain primary aliphatic alkoxylated alcohol.

14. The method of claim 1 wherein said metal alkoxide component is present in said mixture at a molar ratio of about 2:1 with respect to said organosilane component.

* * * * *

UNITED STATES PATENT AND TRADEMARK OFFICE
CERTIFICATE OF CORRECTION

PATENT NO.        : 8,709,545 B2  
APPLICATION NO.   : 12/363085  
DATED             : April 29, 2014  
INVENTOR(S)       : Larson-Smith et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 651 days.

Signed and Sealed this  
Eleventh Day of August, 2015

Michelle K. Lee  
*Director of the United States Patent and Trademark Office*